(12) United States Patent
Bertschi et al.

(10) Patent No.: US 6,467,332 B1
(45) Date of Patent: Oct. 22, 2002

(54) DEVICE FOR OLFACTORY JUDGMENT OF AN ODOROUS SUBSTANCE, USE THEREOF AND A METHOD OF OPERATING THE DEVICE

(75) Inventors: Louis Bertschi, Pfäffikon; Rolf Schwarzenbach, Winterthur, both of (CH)

(73) Assignee: Givaudan SA, Dubendorf (CH)

( * ) Notice: Subject to any disclaimer, the term of this patent is extended or adjusted under 35 U.S.C. 154(b) by 36 days.

(21) Appl. No.: 09/706,018

(22) Filed: Nov. 3, 2000

(30) Foreign Application Priority Data

Nov. 4, 1999 (CH) ............................................... 2020/99

(51) Int. Cl.[7] ............................................. G01N 33/00
(52) U.S. Cl. ..................................... 73/23.34; 73/865.6
(58) Field of Search ........................... 73/23.34, 865.6; 48/195; 261/DIG. 17, 100, 101, 102, 105; 428/905

(56) References Cited

U.S. PATENT DOCUMENTS

| 4,770,027 | A | * | 9/1988 | Ehara et al. | ............... | 73/23.34 |
| 4,981,046 | A | * | 1/1991 | Lawrence et al. | ......... | 73/865.6 |
| 5,115,975 | A | | 5/1992 | Shiling | | |
| 5,328,646 | A | * | 7/1994 | Bryson et al. | ............... | 261/102 |

FOREIGN PATENT DOCUMENTS

| DE | 42 23 263 | 1/1994 |
| DE | 42 39 277 | 6/1994 |
| EP | 238983 | 9/1987 |
| EP | 317299 | 6/1989 |
| GB | 2247623 | 3/1992 |
| GB | 2279010 | 12/1994 |

OTHER PUBLICATIONS

Derwent English language abstract of EP 238983.
Derwent English language abstract of DE 42 23 263.
Derwent English language abstract of DE 42 39 277.

* cited by examiner

Primary Examiner—Daniel S. Larkin
(74) Attorney, Agent, or Firm—Fish & Richardson P.C.

(57) ABSTRACT

A device for olfactory judgement of an odorous substance, particularly a perfume, substantially comprising a flat test object in a casing, preheated or heated electrically by a temperature control and measuring circuit to a given temperature and with prolonged heat storage means, on which an easily attachable and removable material is disposed and is covered with the odorous substance for judgement, the device also comprising a fan, wherein in the casing (2) the odorous substance can be applied to a sample strip (14) connected via a sample holder (12) to a heatable metal base carrier (7) movable in one direction (P), and the base carrier (7) is disposed at one end of an air flow duct (6) formed by a pipe (5), particularly a square pipe (5) open at both ends, a fan (18) being disposed at the other end and adapted, by means of an associated motor (17), to convey air from the end near the fan, via the sample strip (14) to the other end of the air flow duct (6), so that a starting air flow (34a), a received air flow (34b) containing evaporated odorous constituents, and a discharged flow (34c) considered with odorous constituents are generated at the opening (44), so that the odorous substance can be judged by a test person sniffing the discharged flow (34c) through his nose or by collecting the odorous constituents from the discharged flow (34c) and introducing them into a per se known analytical device. The device is adapted to simulate the olfactory properties of an odorous substance on or near human skin.

25 Claims, 3 Drawing Sheets

DEVICE FOR OLFACTORY JUDGMENT OF AN ODOROUS SUBSTANCE, USE THEREOF AND A METHOD OF OPERATING THE DEVICE

FIELD OF THE INVENTION

The invention relates to a device for olfactory judgement of an odorous substance, particularly a perfume. The device contains a flat test object preheated or heated in a casing to a given temperature by electrical heating via a temperature control and measuring circuit and with prolonged heat storage means, on which an easily attachable and removable material is disposed and coated with the odorous substance for judgement. The invention also relates to a device for simulating the properties of an odorous substance or a perfumed fabric on human skin and judgement thereof.

BACKGROUND OF THE INVENTION

A device for olfactory judgement of an odorous substance, particularly a perfume, is known from German Laid-Open Specification 42 39 277 ("DE '277"), which is derived from German Laid-Open Specification 42 23 263. The disclosed device is a flat test object in a casing, preheated electrically via a temperature control and measuring circuit to a given temperature and with a prolonged heat storage means, on which an easily attachable and removable material is disposed and coated with the odorous substance for olfactory testing. Alternatively, preheating or heating can be with hot air, using a fan for uniformly distributing the heat. After an arbitrary residence time at an arbitrary temperature, the test object coated with the odorous substance can be removed from the device and the olfactory judgement can be made.

The known device is used mainly for a method of recognizing and simulating the nature and intensity of the scent from a perfume after various time intervals. For example, the test can show how the odorous substance behaves after an hour at body temperature, i.e. what variety and intensity of scent occurs after one hour. A judgement of this kind is of critical importance both for development and for the characterization of odorous substances. The device is thus also of general use for production and testing, i.e. especially for development of perfumes by perfume manufacturers.

One important disadvantage of the known device is that the test object has to be removed from the device in order to make the olfactory judgement of the odorous substance.

SUMMARY OF THE INVENTION

Accordingly, one object of the invention is to overcome this disadvantage and to provide a more easily operated, mobile device for e.g., judging odorous substances by e.g., professional perfume producers.

Another object of the invention is a device that reproducibly simulates the olfactory properties of an odorous substance or a scented (perfumed) fabric on or near human skin. Another object is to provide a method for judging these properties.

DETAILED DESCRIPTION OF THE INVENTION

Figure 1:
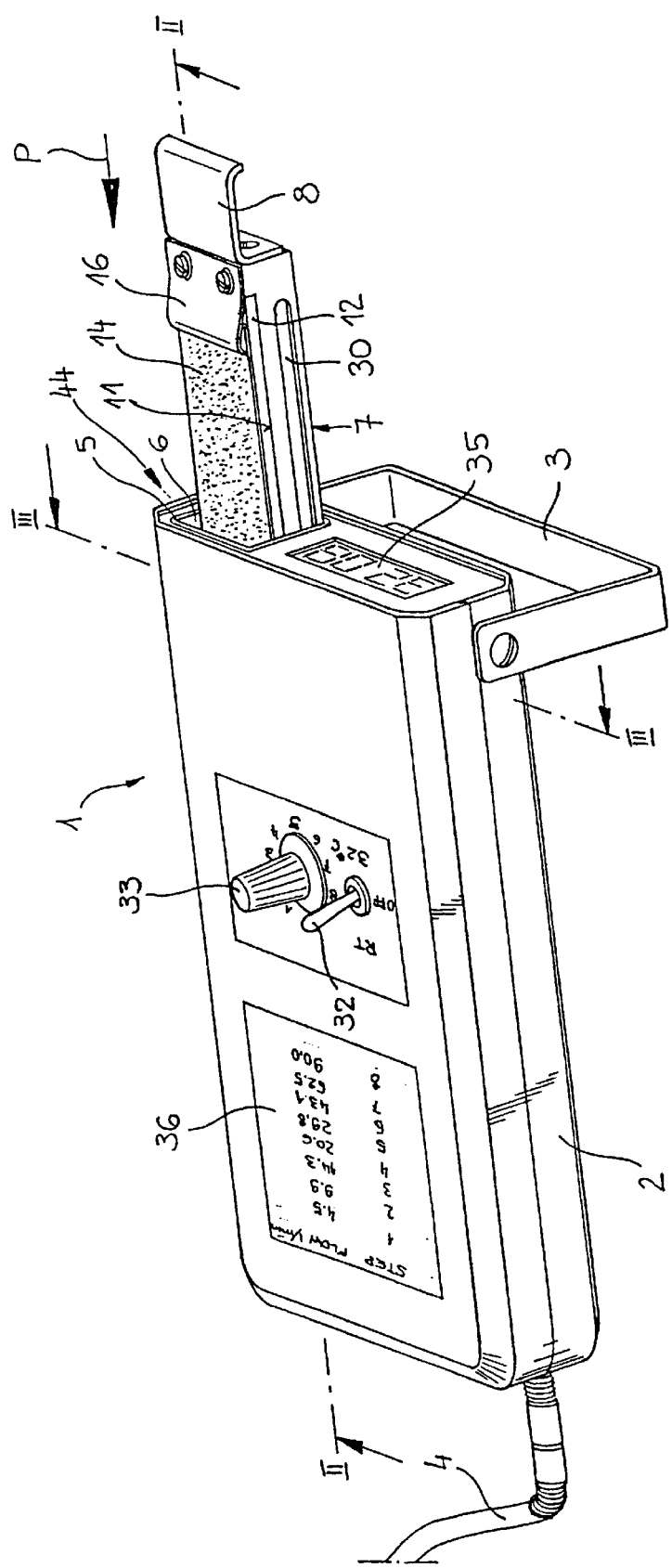
FIG. 1 is a perspective view of a first exemplified embodiment of the device of the present invention.

The device and method according to the invention, for the first time make it possible to simulate the properties of an odorous substance or a scented textile fabric on or near human skin, and to judge its smell under these conditions. The textile fabric can e.g. be a sample of textile from an article of underwear worn next to the skin, after washing and/or rinsing with a perfumed washing and/or rinsing agent. The device is easier to handle than other prior art devices because the odorous substance or scented textile fabric for olfactory judgement does not need any further manipulation of the scented material after simple insertion into the device according to the invention in order to judge its olfactory properties.

As used herein, "odorous substance" means an individual odorous chemical compound, a combination of odorous chemical compounds optionally combined with other chemical compounds, or more particularly combinations containing odorous natural oils, particularly ethereal oils, as in the case of a perfume.

The olfactory properties of an odorous substance on or near human skin cannot be simulated by the device disclosed by DE '277 (even though this is alleged in the Laid-Open specification) because neither a specific temperature is stated nor is its constancy assured. Also, in the DE '277 device there is no simulation of air continuously moving over the skin. Another point is that the temperature of the air moving over the skin is not appreciably increased by the skin temperature, i.e. remains at ambient temperature, usually room temperature, and the odorous substance applied to the skin is judged at this temperature.

Particularly when the simulated olfactory properties of scented fabric have to be judged on or near human skin, i.e. the simulated properties of the scent from a scented article of underwear during use, i.e. when worn, it is particularly important to make the judgement at ambient temperature, since otherwise the odorous substance will be completely incorrectly judged since, as was recognized by the present inventors, the properties of the odorous substance vary considerably at different temperatures, particularly at temperatures above room temperature.

Now turning to the figures, FIGS. 1–4 show a device 1 designed preferably for mobile use. A pipe 5, particularly a square pipe 5 forming an air flow duct 6 is disposed in a casing 2 containing a foldable curved stand 3 in the front region on the underside and an energy supply line 4 on the back. A base carrier 7 containing a handle 8 and an electric plug-in contact 9 for supplying a heating current and temperature control is disposed in the square pipe 5 so as to be releasably movable (arrow P) in the longitudinal direction of the square pipe 5.

A glass sample holder 12 is mounted on the recessed upper receiving surface 11 of the base carrier. On the underside of the base carrier, the sample holder 12 has a meander-shaped heating device 13 electrically connected to the plug-in contacts 9 via lines 13a. The upper surface of the sample holder 12 receives a sample strip 14 fixed by spring clamps 15, 16 to the sample holder 12, which in turn is connected to the receiving surface 11 of the metal base carrier 7.

In the square pipe 5, a motor 17 driving a fan 18 is disposed in front of the base carrier 7 and the contacts 9. The motor 17 is fastened to the end of the pipe 5 via an air guide tube 19 and a flange 21. The motor 17 is secured in the tube 19 by struts 22 to form a substantially annular free flow cross-section 23.

In order to clean the received air flow 34b, a filter member 24 is mounted in front of the fan 18 in order to purify the intaken air. In front of and adjoining the filter is a substantially free space 25 in which a turbulence-free flow field forms for the intaken air flow 34a sucked through the openings 26. The air conveyed through the fan 18 can be adjusted by a stepwise or a continuously operated control means for the motor 17, via a rotary knob 33 on the top of the casing. The air flow rate may be adjusted in the range from 2–2000 ml/min., preferably in the range from 10–100 ml/min.

Figure 2:
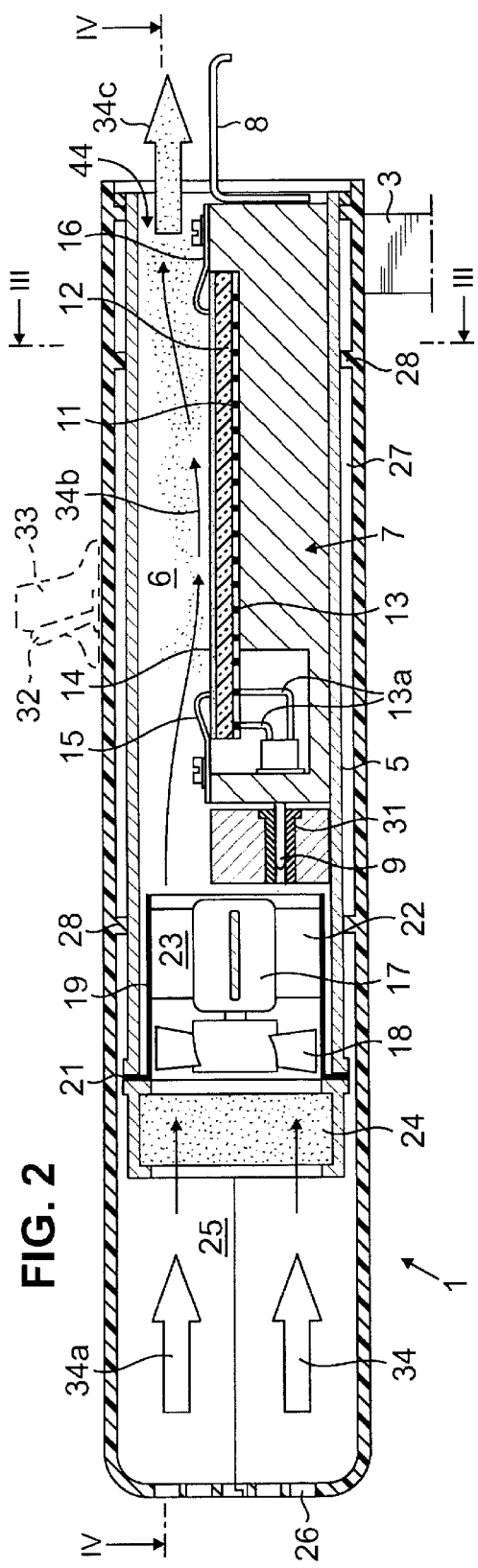
FIG. 2 is a longitudinal section in the plane II—II of FIG. 1.

As shown particularly in FIG. 2, the square pipe 5 is mounted in the casing 2 on spacer ribs 28, forming a thermally insulating air gap 27. It is thus possible, in conjunction with the high metallic mass of the base carrier 7, to maintain a constant uniform temperature at the surface of the sample holder 12 and scented sample strip 14. The sample strip 14 is more particularly a cellulose strip, or alternatively a suitably dimensioned piece of scented textile fabric can be placed on the sample holder 12. In addition, a number of sample strips 14, for example two strips, bearing different odorous substances can be placed on the sample holder 12, in order to judge the combined effect of the odorous substances.

The device in FIGS. 1 to 4 operates in general as follows: the base carrier 7 and sample holder 12 are pulled out of the square pipe 5, using the handle 8. The odorous substance for analysis is applied in the form of an alcoholic solution to the sample strip 14, preferably a cellulose strip, such as a cellulose strip having a weight per unit area of 300 g/m$^2$. The amount of alcoholic solution applied to the strip is about 2–20 $\mu$l/cm$^2$ of the sample strip 14, preferably 3–5 $\mu$l/cm$^2$ of the sample strip 14. The alcoholic solution contains the odorous substance in a concentration of from 1% (wt) to nearly 100% (wt), preferably 10% (wt)–20% (wt).

Figure 3:
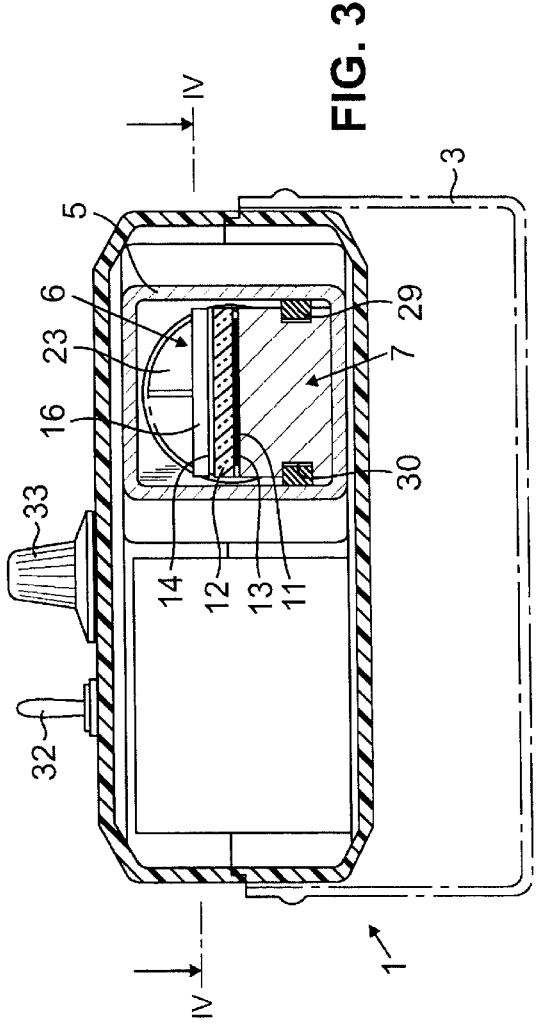
FIG. 3 is a cross-section in the plane III—III of FIGS. 1 and 2.

The sample strip 14 is already fastened to the sample holder 12 by the two spring clamps 15, 16. As shown particularly in FIG. 1, the unit (7, 12, 14, 15, & 16) containing the odorous substance can be inserted in the direction of arrow P into the square pipe 5 or into the air flow duct 6. As shown in FIG. 3, the base carrier 7 is reliably guided by parallel grooves 30 on the base carrier 7 and guide rails 29 inside the square pipe 5.

The base carrier 7 is inserted until the electric plug-in contacts 9 are in full electric contact with and abutting the sockets 31. By means of a switch 32 on the top of the casing, the device is switched on and the heating stage is preset, i.e. at the temperature produced by the heating device 13 at the surface of the sample holder 12, preferably for simulating the human skin surface temperature, i.e. at about 32° C.

After or before operating the switch 32, the motor 17 and consequently the fan 18 are started up by a rotary knob 33 on the top of the casing, e.g. at "ventilation stage 5." Thus, a constant air flow of 30 ml/min. is conveyed so that the sample strip 14, preferably having an area of 2×5 cm and covered with preferably 3–5 $\mu$l/cm$^2$ of alcoholic solution preferably containing 10–20% (wt) odorous substance, and non-positively connected by the spring clamps 15, 16 to the sample holder 12, which is in close operative connection with the base holder 7, is swept by the air flow in order to simulate the properties of a corresponding amount of the odorous substance applied in a normal manner to human skin when the test person is engaged in moderate activity. The air is substantially unheated, which is an important criterion in the simulation.

The intaken air stream 34a at room temperature is sucked in through the fan 18 and conveyed along the air flow duct 6. The received air stream 34b, practically without increase in temperature, continuously absorbs evaporated constituents of the odorous substance from the sample strip 14. The discharged air 34c comes out substantially at room temperature from the opening 44, where it can be judged or at an interval of up to about 1 m by direct smelling by the perfume manufacturer or, if required, after previous trapping (absorption) in an analytical device.

Instead of a switch 32 for a fixed heating-stage adjustment, the temperature adjustment can be varied or controlled in a number of stages, via a potentiometer operated by a rotary knob 33. The advantage of the design according to the invention can be immediately understood. Owing to the correspondingly higher temperatures and higher ventilation stages, a correspondingly higher air flow 34 or a higher evaporation temperature can be set, thus increasing the evaporation rate so that the analysis can be speeded up or directed towards a given range of scents (e.g. body or base variety). The operating conditions, such as the temperature and ventilation stages, can be read off a display 35. The preferred ventilation stages can be shown in user-friendly way on a table 36 on the top surface of the casing 2.

Figure 4:
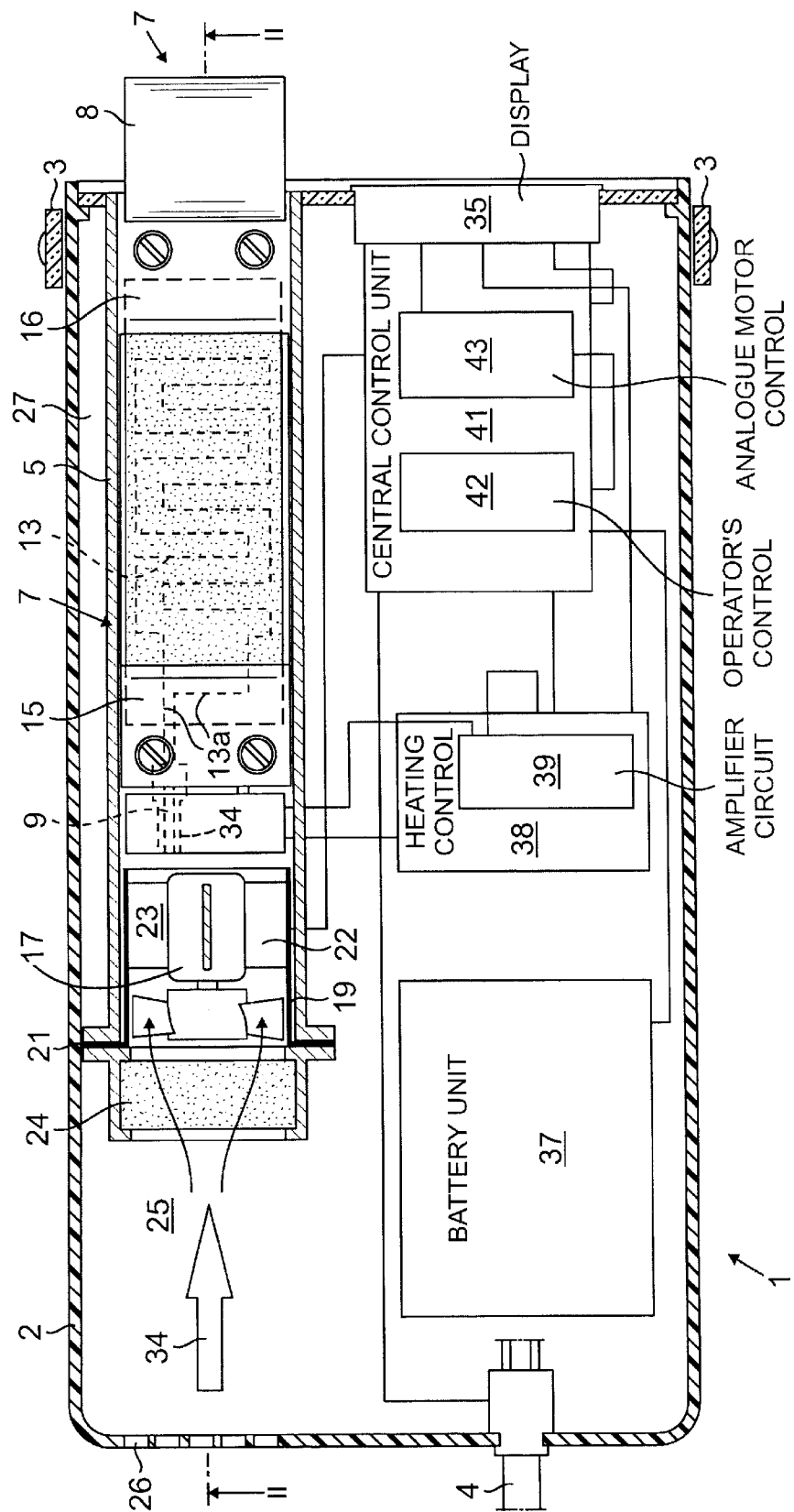
FIG. 4 is a horizontal section in the plane IV—IV of FIGS. 2 and 3.

FIG. 4 shows a battery unit 37 in cases where the device has to operate independently of the main power source. Reference 38 denotes an electronic automatic heating control device and 39 denotes an amplifier circuit for the temperature control means. Reference 41 denotes the central control unit, 42 the operator's control, and 43 denotes the analogue control system for the motor 17 or the blower.

The invention being thus described, it will be obvious that the same may be varied in many ways. Such variations are not to be regarded as a departure from the spirit and scope of the invention and all such modifications are intended to be included within the scope of the following claims.

What is claimed is:

1. A device for olfactory judgment of an odorous substance comprising a flat test object in a casing, preheated or heated electrically by a temperature control and measuring circuit to a given temperature and with prolonged heat storage means, on which an easily attachable and removable material is disposed and is covered with the odorous substance for judgment, wherein the casing (2) the odorous substance can be applied to a sample strip (14) connected by a sample holder (12) to a heatable metal base carrier (7) movable in one direction (P), wherein the base carrier (7) is disposed at one end of an air flow duct (6) formed by a pipe (5) open at both ends, a fan (18) disposed at the other end and adapted, by means of an associated motor (17), to convey air from the end near the fan, via the sample strip (14) to the other end of the air flow duct (6), so that an intaken air flow (34a), a received air flow (34b) containing evaporated odorous constituents, and a discharge flow (34c) are directed through an opening (44).

2. A device according to claim 1, wherein the odorous substance is a perfume.

3. A device according to claim 1 wherein the pipe is a square pipe.

4. A device according to claim 1 wherein the base carrier (7) can be removed from the air flow duct (6) before applying an odorous substance to the sample strip (14).

5. A device according to claim 1 wherein the sample holder (12) is made of glass.

6. A device according to claim 1 wherein the sample strip (14) is a cellulose strip or a perfumed fabric.

7. A device according to claim 1 wherein a heating device (13) connected to an automatic heating control unit (38) is disposed on the side of the base carrier (7) associated with the sample holder (12) and can heat the sample strip (14) uniformly.

8. A device according to claim 7 wherein the sample strip is heated up to a higher-evaporation temperature.

9. A device according to claim 8 wherein the sample strip is heated from about room temperature to about 50° C., and is maintained at a selected temperature between room temperature and about 50° C.

10. A device according to claim 1 wherein the motor (17) is variably operated, continuously operated, or stepwise operated, so that the amount of air conveyed over the sample strip (14) is adjustable.

11. A device according to claim 10 wherein the amount of air conveyed over the sample strip (14) is in the range from 2–2000 ml/min.

12. A device according to claim 1 wherein a filter member (24) is mounted in front of the fan (18) for cleaning an intaken air flow (34a).

13. A method for simulating olfactory properties of an odorous substance on or near the human skin comprising applying an odorous substance to a device according to claim 1.

14. A method according to claim 13 wherein the odorous substance is a perfume.

15. A method for simulating olfactory properties of an odorous substance on or near the skin of a test person engaged in moderate activity comprising applying an odorous substance to a sample strip in the device of claim 1 and heating the sample strip to skin surface temperature, and conveying a constant air flow over the sample strip (14).

16. A method according to claim 15 wherein sample strip is maintained at about 32° C., and a constant flow of air is conveyed over the sample strip at a rate of about 30 ml/min.

17. A method according to claim 15 wherein the odorous substance on the sample holder (14) is applied in the form of an alcoholic solution in a proportion of 2–20 $\mu$l/cm$^2$ surface area of the sample strip (14).

18. A method according to claim 17 wherein the alcoholic solution is in a proportion of 3–5 $\mu$l/cm$^2$ surface area of the sample strip (14).

19. A method according to claim 17 wherein the alcoholic solution contains the odorous substance in a concentration from 1% (wt) to almost 100% (wt).

20. A method according to claim 19 wherein the alcoholic solution contains the odorous substance in a concentration from 10% (wt) to 20% (wt).

21. A method according to claim 15 wherein the sample strip (14) is a cellulose strip.

22. A method according to claim 21 wherein the cellulose strip has a weight per unit area of 300 g/m$^2$.

23. A method according to claim 15 wherein the sample strip (14) is a piece of perfumed textile fabric.

24. A method according to claim 15 wherein the sample strip (14) has an area of 2×5 cm.

25. A device for measuring an olfactory effect of an odorous substance comprising:

(a) a casing (2);

(b) a pipe (5) disposed within the casing and forming an air flow duct (6) with a front end that opens at the front of the casing and a back end opening, the pipe being adapted to accommodate a base carrier (7);

(c) a base carrier having a recessed upper receiving surface (11) and an underside, the base carrier being releasably moveable within the pipe, the base carrier comprising a handle (8) on one end of the base carrier, an electric plug-in contact (9) on an under surface of the carrier and on the opposite end of the base carrier from the handle, for supplying a heating current and a temperature control;

(d) a sample holder (12) having an upper surface and a lower surface, the sample holder being mounted on the recessed upper receiving surface (11) of the base carrier, the sample holder having a heating device (13) electrically connected to the plug-in contact on the carrier via electrical lines (13a), wherein the upper surface of the sample holder is adapted to receive a sample strip containing an odorous substance which is detachably affixed to the sample holder; and (e) a motor (17) in electrical connection with a fan, the motor disposed in front of the base carrier and plug-in contact and affixed to the back end of the pipe via a guide tube and a flange, the motor being secured to the guide tube by struts to form a substantially annular free flow cross-section, wherein the fan conveys air through the pipe and over the sample holder and sample strip and the discharged air flow exists through the front end opening of the pipe.

* * * * *